United States Patent [19]

Olin et al.

[11] 3,983,743

[45] Oct. 5, 1976

[54] APPARATUS AND METHOD FOR THE ANALYSIS OF A PARTICLE-LADEN GAS

[75] Inventors: John George Olin, St. Paul; Virgil Alan Marple, Minneapolis, both of Minn.

[73] Assignee: Sierra Instruments, Inc., Carmel Valley, Calif.

[22] Filed: Sept. 19, 1973

[21] Appl. No.: 398,875

[52] U.S. Cl. .................................... 73/28; 55/270
[51] Int. Cl.² ........................................ G01N 15/02
[58] Field of Search .......... 73/28, 432 PS, 421.5 R, 73/421.5 A; 55/446, 445, 465, 462, 485, 270

[56] References Cited
UNITED STATES PATENTS

| | | | |
|---|---|---|---|
| 1,857,348 | 5/1932 | Bokenkroger | 55/446 |
| 3,001,914 | 9/1961 | Andersen | 73/28 X |
| 3,222,925 | 12/1965 | Kracke et al. | 73/28 X |
| 3,576,721 | 4/1971 | Mason | 73/28 X |
| 3,606,738 | 9/1971 | Kraus | 55/446 |
| 3,693,457 | 9/1972 | Pilat | 73/28 |
| 3,795,135 | 3/1974 | Andersen | 73/28 |

FOREIGN PATENTS OR APPLICATIONS

| | | | |
|---|---|---|---|
| 59,559 | 1/1942 | Denmark | 55/485 |

OTHER PUBLICATIONS

*Chemical Engineering Progress,* "Three Multi-Stage Stack Samplers," Holland et al., vol. 69, No. 6, June 1973, pp. 93-95.
*Journal of Nuclear Science and Tech.,* "Performance of an Improved Air Sampler," Fukuda et al., vol. 7, No. 9, Sept. 1970, pp. 450-457.
*Applied Microbiology,* "Novel Multi-Slit Large Volume Air Sampler," Buchanan et al., vol. 16, No. 8, Aug. 1968, pp. 1120-1123.

*Primary Examiner*—Richard C. Queisser
*Assistant Examiner*—Stephen A. Kreitman
*Attorney, Agent, or Firm*—Gary L. Griswold

[57] ABSTRACT

An apparatus for the collection of particles from a gas containing particles which comprises a first means for directing the flow of said gas toward a second means for collection of at least a portion of said particles by the process of impaction, the first means containing inlet means which comprises at least one perforation having a length dimension which is greater than its width dimension and a third means between and contacting said first and second means and having an inner wall, which is a smooth closed curve, the third means being located relative to the inlet means and the third means having a configuration such that a substantial number of the streamlines of the flow of said gas after the impaction of at least a portion of said particles in said gas with the second means are in substantial parallelism to the curve of the wall of the third means; the first, second and third means forming an enclosed volume having the inlet means and outlet means for exit of the gas after the impaction of at least a portion of the particles in the gas with the second means.

17 Claims, 10 Drawing Figures

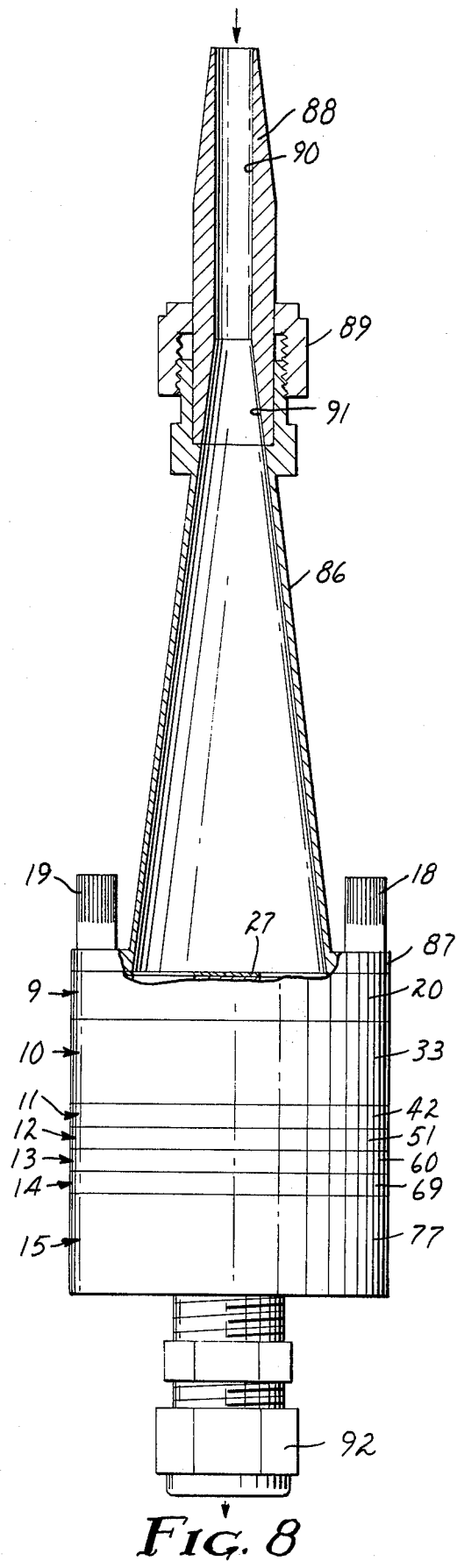
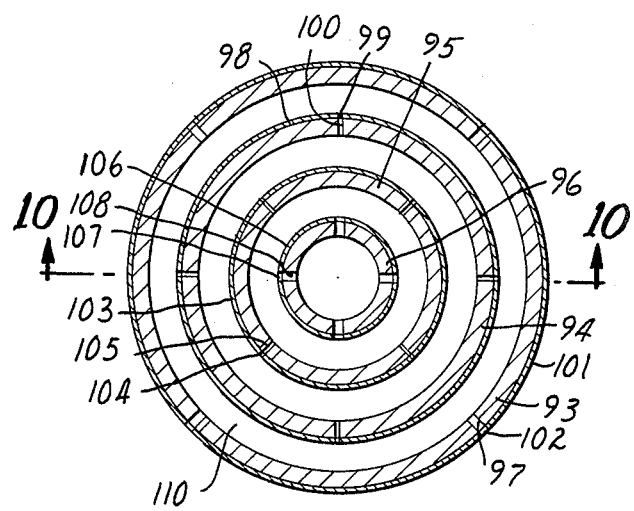
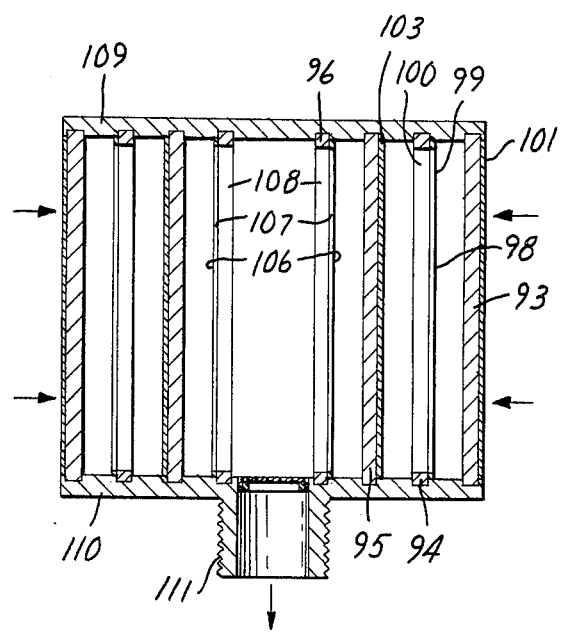
FIG. 8
FIG. 9
FIG. 10

APPARATUS AND METHOD FOR THE ANALYSIS OF A PARTICLE-LADEN GAS

This invention relates to an apparatus for analysis of the size distribution of particles suspended in a gas and for fractionating and collecting said particle by size. In particular, this invention relates to an apparatus for such analysis which contains means to orient the streamlines of the flow of the gas after each successive impaction of a portion of the particles suspended in the gas so that a substantial number of the streamlines are in substantial parallelism to the inside wall of the apparatus; thus, particle losses by secondary impaction are reduced.

An impactor is an instrument which samples an aerosol, i.e., a gas in which solid or liquid particles are suspended. The impactor size-fractionates the particles in the gas by means of accelerating the aerosol through one or more nozzles of circular, rectangular, or other, cross-section and impacts a portion of the particles onto a collection surface. By virtue of their inertia, particles greater than a characteristic cut-off size of the impactor have trajectories which depart sufficiently from the turning streamlines of the gas flow and strike, or impact on the collection surface and thereby are collected. The cut-off size of an impactor stage primarily depends on the inertial and aerodynamic forces acting on the particle, which in turn depend on the size, shape and specific gravity of the particles and on the velocity and properties of the gas medium. Impactors are most often used to separate particles by size, since the other parameters usually are known or can be adequately estimated.

Single-stage and cascade, that is, multiple-stage impactors are known. (See British Pat. No. 659 for a single-stage impactor using a single circular nozzle.) A single-stage impactor using a plurality of nozzles, that is, 300 circular holes, is discussed in an article entitled, "A Sieve Device For Sampling Air-Borne Microorganisms," by H. L. DuBuy and L. R. Crisp, *Public Health Reports*, Vol. 59, June 30, 1944, No. 25, pp. 829–832. U.S. Pat. No. 2,538,116, discloses a "cascade impactor" in which several impactor stages are assembled in a series. Each stage of the cascade impactor consisted of a single, nearly rectangular nozzle. The size of the nozzles were successively reduced in size from stage to stage. Therefore, the jet velocity and the inertia of the particles increase progressively from stage to stage, with the result that each successive stage has a smaller particle cut-off size. The cascade impactor therefore fractionated the particles by size. U.S. Pat. No. 3,001,914 discloses a cascade impactor for collecting viable particles, wherein each nozzle stage consisted of several hundred circular holes and the collection surface consisted of a dish containing a nutrient medium.

A major source of inaccuracy in single or multi-stage impactors is the deposition of particles on surfaces of the impactor other than the collection surfaces, a phenomenon often called "iner-stage loss." This phenomenon reduces the sharpness of the particle collection efficiency curves for the impactor stages and reduces the accuracy of measurement of total particle mass concentration and of the size-fractionation of particles since such losses cannot be accurately estimated for different aerosols. Inter-stage loss is commonly caused by the impaction of particles on extraneous surfaces by virtue of the existence of aerosol velocity components in the impactor which are normal to portions of the extraneous surfaces.

An impactor has been found which reduces inter-stage losses in impactors and thereby improves measurement accuracy. It is an apparatus for collection of particles from a gas containing particles which comprises a first means for directing the flow of said gas toward a second means for collection of at least a portion of said particles by the process of impaction, said first means containing inlet means which comprises at least one perforation having a length dimension which is greater than its width dimension and a third means between and contacting said first and second means and having an innerwall which is a smooth, substantially closed curve, said third means being located relative to said inlet means and said third means having a configuration such that a substantial number of the streamlines of the flow of said gas after said impaction of at least a portion of said particles in said gas with said second means are in substantial parallelism to the curve of said wall of said third means; said first, second and third means forming an enclosed volume having said inlet means and outlet means for exit of said gas after said impaction of at least a portion of said particles in said gas with said second means. The apparatus can be single or multiple-stage and can be used for collection of liquid or solid particles.

The drawings are briefly described below:

FIG. 8 is a partial section of an apparatus used in the collection of particles from a moving gas stream.

FIG. 9 is a top view of another embodiment of the invention with the upper plate removed.

FIG. 10 is a section of FIG. 9.

Figure 1:
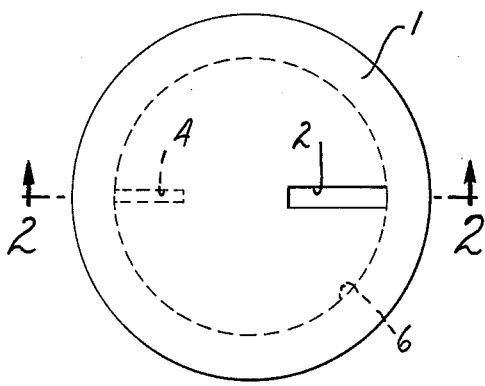
FIG. 1 is the top view of a single impactor stage.

FIG. 1 will be used to describe the principle in the invention. The apparatus shown in FIG. 1 comprises a circular plate 1 containing a perforation 2. Circular plate 3 has an area under perforation 2 of plate 1 for impaction of at least a portion of the particles in the gas flowing through perforation 2 and also contains perforation 4 which is the outlet. Plate 1 and plate 3 are separated from each other by spacer 5. Spacer 5 is a smooth closed curve which in this case is circular, i.e., is an annulus but could be other forms of smooth closed curves. In operation, a gas laden with particles is accelerated through perforation 2 by means of a vacuum pump or vacuum source. Particles of the appropriate size impact on plate 3 below perforation 2 of plate 1 and form a deposit. After impingement on plate 3, the gas flows to perforation or outlet 4 such that a substantial number of the streamlines of the flow of the gas are in substantial parallelism to the innerwall 6 of spacer 5, which is the smooth closed curve. This substantial parallelism of the streamlines of the flow eliminates the inter-stage losses described above. As used herein, a substantial number means at least a majority, and preferably substantially all of the streamlines.

Figure 2:
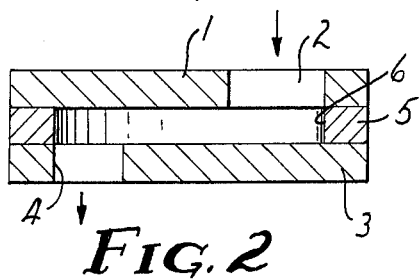
FIG. 2 is a section of the impactor stage of FIG. 1.
Figure 5:
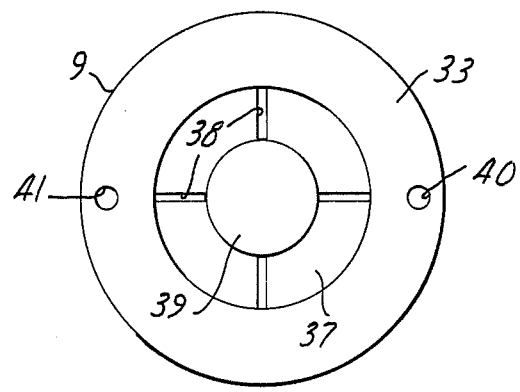
FIG. 5 is a bottom view of the second stage of the impactor shown in FIG. 3.

The assembly shown in FIGS. 1 and 2 can be the basic element of a single stage impactor or of a cascade impactor. In the single stage impactor situation, the gas passes through perforation 4 directly to the vacuum supply or through some intervening element in the gas sampling system. In the cascade impactor situation, perforation 4 is normally in one of two forms:

1. perforation 4 can be a nozzle of a smaller size than perforation 2 and is used to accelerate the remaining particles and collect a portion of them on a subsequent collection surface or
2. perforation 4 can lead to another impaction stage, in which case, the size of perforation 4 is normally much larger than perforation 2 to avoid loss of particles by impaction.

Perforations 2 and 4 can have any cross-sectional shape in which the length dimension is greater than the width dimension. The preferred cross-sectional shape is rectangular. The preferred orientation of the perforation is radial for this allows for symmetry and also substantially eliminates normal velocity components towards the inner wall 6 of the apparatus. The innerwall 6 is a smooth curve which can be any shape, but is preferably circular for this is the most practical and is symmetrical.

A plurality of perforations 2 and 4 can be used. An equal number of perforations 2 and perforations 4, staggered and spaced, at equal angular intervals, has the advantage of symmetry and avoids the problem of interferences between the streamlines of the flow of the gas issuing from the perforations 2. A plurality of smaller perforations 2, rather than a single, large perforation 2 has the advantage of reducing the flow velocity necessary to achieve a given cut-off size, thereby reducing the potential for reintrainment of deposited particles.

Figure 3:
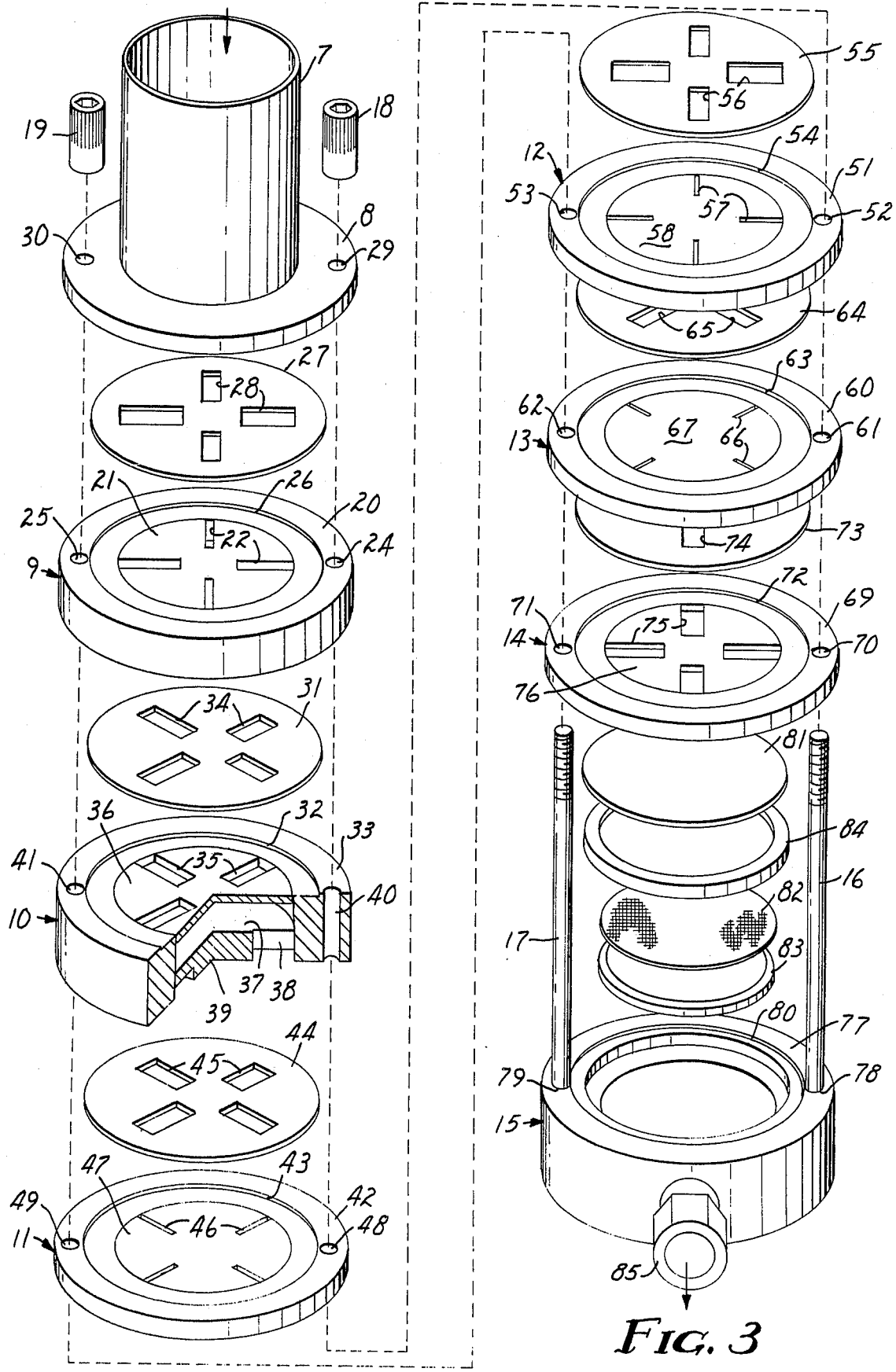
FIG. 3 is a perspective of the preferred embodiment of the multiple-stage impactor of the present invention.

A preferred embodiment of the invention will now be described in regard to FIGS. 3 through 7. The apparatus shown in FIG. 3 is a multi-stage impactor and is shown in perspective. It is used to sample particles suspended in an essentially stagnant gas, such as ambient air. The apparatus consists of inlet tube 7, which is attached to top plate 8. This is followed by subsequent stages 9, 10, 11, 12, 13 and 14 and base 15. These cylindrical stages are sandwiched together between the top plate 8 and base 15 under compression by means of the threaded studs 16 and 17 and nuts 18 and 19. The first stage 9 of the apparatus consists of outer ring 20 into which is press-fit perforation plate 21, containing 4 radial rectangular perforations 22 or slots and hub 23. The perforations 22 are cut into plate 21 by means of a slitting saw and plate 21 is press-fit into or otherwise attached to outer ring 20. The method of construction and assembly results in a nearly true rectangular perforation, thereby avoiding unpredictable end-effects, flow disturbances or other abnormalities. The remaining perforations and slots in the impactor described have this same type of construction. Outer ring 20 has clearance holes 24 and 25 to accommodate threaded studs 16 and 17 and has recess 26 to accommodate collection paper 27, which has slots 28, which are positioned to expose perforations 22 on stage 9. Top plate 8 has clearance holes 29 and 30 to also accommodate the threaded studs 16 and 17. The outer stages likewise have such clearance holes.

The second stage of the apparatus 10 has a different construction than the first stage 9. Collection paper 31 fits in recess 32 of outer ring 33 of stage 10. Collection paper 31 has four large rectangular slots 34 which are oriented 45° from the perforations 22 of stage 9. The slots 34 of collection paper 31 expose the perforations 35 of plate 36 of stage 10. The axes of the perforations 35 stage 10 are oriented 45° to the axes of the perforations 22 of stage 9. Plate 37 with four radial rectangular perforations 38 and hub 39 is also attached to outer ring 33 of stage 10. The axes of perforations 38 are oriented 45° to the axes of perforations 35. Outer ring 33 contains clearance holes 40 and 41. Collection paper 31 is positioned to expose perforations 35. Perforations 35 are much larger than perforations 22 in the first impactor stage 9. The size of perforations 38 in the second impactor stage 10 are smaller than perforations 22 in the first stage 9.

The succeeding impactor stages 11, 12, and 13 are similar to the first impactor stage 9, but the size of the four radial rectangular perforations decreases progressively from stage to stage. The axes of the perforations of any two adjacent stages are 45° apart. Stage 11 has outer ring 42 containing recess 43 for collection paper 44, which contains slots 45, which are oriented 45° from the perforations 38 of stage 10. These slots 45 expose perforations 46 in plate 47 of stage 11. Outer ring 42 contains clearance holes 48 and 49. Plate 47 contains hub 50.

Stage 12 contains outer ring 51 which contains clearance holes 52 and 53 and a recess 54 which holds collection paper 55 containing slots 56 which are oriented 45° from the perforations 46 of stage 11. The slots 56 of the collection paper 55 expose perforations 57 of plate 58 of stage 12. Plate 58 of stage 12 contains a hub 59.

Stage 13 contains outer ring 60 which contains clearance holes 61 and 62 and recess 63 which holds collection paper 64 containing slots 65. The slots 65 of collection paper 64 are oriented 45° from the perforations 57 of stage 12. The slots 65 of collection paper 64 are oriented to expose perforations 66 of plate 67 of stage 13. The perforations 66 are shorter in length than those of any of the previous stages. Plate 67 contains hub 68.

Stage 14 consists of an outer ring 69 which contains clearance holes 70 and 71 and recess 72 for collection paper 73. Collection paper 73 contains slots 74 which are oriented 45° from the perforations 66 of stage 13. The slots 74 of collection paper 73 are oriented to expose perforations 75 of plate 76 of stage 14. The perforations 75 are large rectangular slots. Stage 14 contains no hub. Base 15 consists of an outer ring 77 which contains holes 78 and 79 for attachment of threaded studs 16 and 17. Base 15 also includes recess 80 for filter paper 81. Base 15 also holds screen 82 which is held in by means of rings 83 and 84. The base 15 also contains hose fitting 85 which is connected with a vacuum hose to the vacuum pump or vacuum supply. Filter paper 81 collects almost all of those particles which are smaller than the critical cut-off size of stage 13. The collection paper for all stages is identical. The collection papers and filter paper 81, besides collecting particles, seal the impactor from leaks.

When suction is applied to hose fitting 85, the gas containing the particles to be sampled is drawn into inlet tube 7 and through the four radial rectangular slots 28 of collection paper 27 and four radial rectangular perforations 22 of stage 9. In cases where very large particles are present, some of them may deposit on collection paper 27 and not enter perforation 22. In many cases, collection paper 27 can be omitted. The gas is then accelerated through perforations 22 and particles greater than the cut-off size of the front stage 9 are deposited on collection paper 31 by the process of impaction. The gas then flows to slots 34 in collection paper 31 and through perforations 35 of plate 36 in stage 10. The streamlines of the flow after impaction with collection paper 31 are defined by and are substantially parallel to the inside wall of the outer ring 20, the outer wall of the hub 23, the bottom wall of plate 21 and the top surface of collection paper 31. Loss of particles to all surfaces of the channel by process of impaction is substantially eliminated. Small losses to the surfaces of said channels may be caused by turbulent eddy motion of the gas and/or small losses to the inside wall of outer ring 20 may be caused by the action of centrifugal forces on the particles. The gas with the remaining portion of the small particles then enters the second stage 10 through perforations 35 which are sufficiently large in size to make negligible the loss of particles by impaction on the top surface of plate 37. The gas then flows circumferentially without impaction loss to four radial slots 38. The gas is accelerated through perforations 38, and the remaining particles greater than the cut-off size of the stage 10 are deposited on collection paper 44. The gas flows circumferentially to the four radial rectangular slots in the third stage 11 and is accelerated through perforations 46 and particles contained therein are impacted on the collection paper 55. The gas, in like means, flows through stages 12 and 13. The particles leaving stage 13 are deposited on collection paper 73. The gas then flows circumferentially to slots 74 in the collection paper 73 and through perforation 75 in stage 14. All remaining particles smaller than the cut-off size of the last stage 13 are collected with high efficiency by filter paper 81. In some cases, filter paper 81 and screen 82 are removed from the cascade impactor and the remaining fine particles are collected in a separate downstream filter or are ignored altogether.

The apparatus can merely have a number of successive stages, such as stages 9, 11, 12 and 13 in which the plate containing the accelerating perforations and the collection plate are synonymous. This design is advantageous because of its simplicity and because it minimizes the volume of the impactor and thereby minimizes inter-stage particle loss by the process of diffusion and sedimentation. It has been found that it is beneficial to include stage 10 as the second stage in the apparatus. This is not required but is advantageous. This stage 10 has a plate 37 containing the accelerating perforation which is separate from the collection plate, i.e., plate 36. It has been found that if stage 10 is constructed in a similar manner to the remaining stages, the particle deposit of stage 10 can be slightly non-uniform under certain combinations of flow rate and particle characteristics. Non-uniformity is negligible if the stage 10 is included. It is preferred to have the axis of the perforations 38 oriented 45° from the axis of the perforations 35. These axes can be concurrent, but the possibility of inter-stage losses is increased if they are concurrent.

Figure 7:
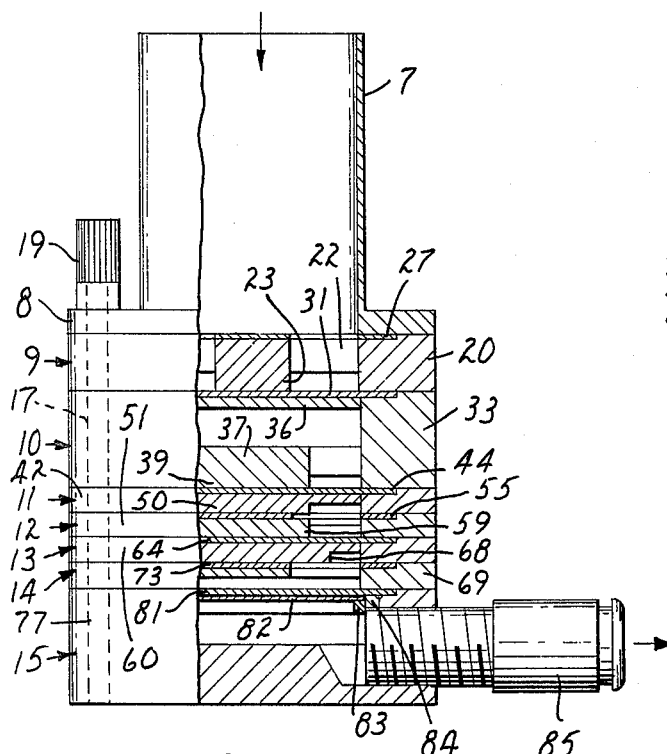
FIG. 7 is a side view with portions in section of the apparatus shown in FIG. 3 and 6.
Figure 6:
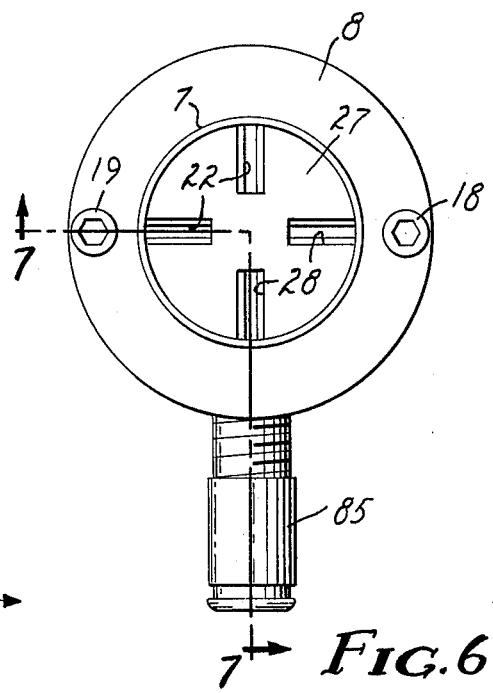
FIG. 6 is a top view of the apparatus shown in FIG. 3.
Figure 4:
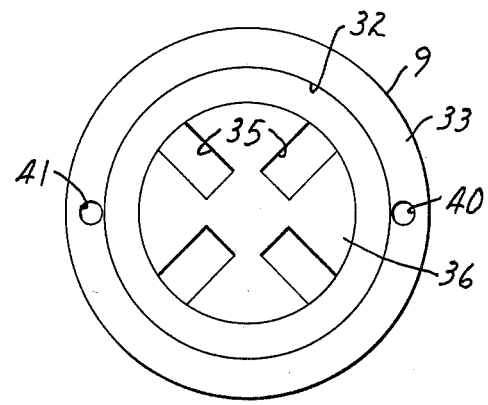
FIG. 4 is a top view of the second stage of the impactor shown in FIG. 3.

The collection papers as shown in FIGS. 3, 6 and 7 are constructed of glass fiber, filter paper or other material, such as aluminum foil. If desired, the collection papers can be omitted. Deposition of the particles on the collection papers instead of directly on the impactor stages themselves has the advantages of reducing particle reintrainment which is a major problem with previous impactors, lowering the cost of conducting successive tests, allowing easy storage and subsequent chemical analysis, reducing the tare weight, and eliminating the need for coatings which adulterate the sample. The impactors of this invention are normally made of metal, preferably stainless steel or aluminum, but can be made from other materials such as plastic.

FIG. 8 shows a section view of another embodiment of the invention consisting of the apparatus as discussed above with a different inlet tube and vacuum tube connection. This embodiment is useful for sampling particles suspended in a moving gas stream, such as in a stack, which conveys particulate air pollution emissions.

In FIG. 8, a transition section 86 is attached to top plate 87 of the apparatus. Sampling nozzle 88 is attached to transition section 86 by means of tube fitting 89. The sampling nozzle is removable and can be replaced, by other sampling nozzles with different inlet sizes. The sampling nozzle has a straight portion 90 which blends into flared portion 91. The apparatus is connected to a vacuum pump, vacuum source, or particulate sampling system by means of tube fitting 92. The remainder of the embodiment of the invention is identical to the first embodiment described above in reference to FIGS. 3 through 7.

In operation, the apparatus shown in the FIG. 8 is positioned directly in the moving gas stream with the sampling nozzle 88 facing into the stream and with the axis of the apparatus parallel to the flow velocity. When suction is applied to fitting 92, the gas is drawn into the sampling nozzle 88, passes through transition section 86 and enters the first stage of the impaction apparatus. Thereafter, the operation of the apparatus is similar to that discussed above in reference to FIGS. 3 through 7. Representative sampling of the particles in the moving gas stream is accomplished by means of isokinetic sampling which is defined as the condition in which the velocity of the gas stream is identical to the velocity of the sampled gas just as it enters the sampling nozzle 88. In this way, a proportional gas sample is extracted from the main stream. Isokinetic sampling is achieved by selecting the proper sampling flow rate and the sampling nozzle 88 with the proper inlet size.

The apparatus shown in FIG. 8 can be used for inline sampling applications. In that instance, the sampling nozzle 88 is removed and a tube leading to the gas source is inserted into tube fitting 89.

The impactors of the present invention can be operated at a flow rate of normally about ½ to ¾ cubic feet per minute, but can be varied from 0.3 to 1 cubic feet per minute (CFM) to achieve isokinetic sampling. By changing the number and size of the perforations and the size of the apparatus, one can easily adapt the apparatus to different flow requirements such as from 1 to 2 liters per minute for attachment to the lapel of clothes worn by personnel or to much larger versions for operating from 20 to 60 CFM for attachment to the standard high volume sampler or for operation at high flow rates. The normal operating pressure of the apparatus is approximately one atmosphere. Low pressures can be used to reduce the cut-off sizes of the impactor stages.

Another embodiment of the invention is shown in in FIGS. 9 and 10. In this case, the apparatus is a series of cylinders of decreasing diameter. In FIG. 9, these cylinders are represented as separate stages 93, 94, 95 and 96. Stage 93 contains perforations 97 through which flows the gas containing the particles. The gas then impacts on collection paper 98 which is around stage 94. The filter paper 98 has perforations 99 which correspond to the perforations 100 of stage 94. Stage 93 also has collection paper 101 surrounding it, with perforations 102 uncovering its perforations 97. The perforations 97 of stage 93 are 45° from those of stage 94. Stage 95 is likewise surrounded by collection paper 103 containing perforations 104, which expose perforations 105 of stage 95. Stage 96 is surrounded by collection paper 106 with perforations 107 which expose perforations 108 of stage 96. Plates 109 and 110 hold these cylinders and filter papers in position. The apparatus is attached to a vacuum source or vacuum pump through hose connection 111.

In operation, a vacuum is applied through hose connection 111 and the gas containing particles first contact the collection paper 101 and any very large particles remain on that paper. The flow then moves through perforations 102 of collection paper 101 and through perforations 97 of stage 93. A portion of the particles as discussed above with reference to the other embodiment described is then impacted on the collection paper 98 surrounding stage 94 at a point on collection paper 98 corresponding to the perforations 97 of stage 93. The flow then moves through perforations 99 and collection paper 98 of stage 94 and then through perforations 100 of stage 94 and so on through the remainder of the stages and out tube fitting 111. A cylindrical filter paper with a cylindrical support can be included in the inside of the final stage 96. The flow in this embodiment also has a substantial number of streamlines which are substantially parallel to the wall of the stage from whence the flow did come, to the next succeeding stage and to plates 109 and 110, and thus, inter-stage losses would be negligible.

The apparatuses shown in FIGS. 1 to 10 have the additional advantage of having no end or edge effects. The radial slots of the apparatus in FIG. 3 to 8 are symmetric, i.e., the slots continuously repeat and in no case, is the longest dimension of any slot adjacent to or near a wall. This is contrasted to an impactor having a plurality of parallel slots, in which case at least one of the extreme or edge slots must be adjacent to or near a wall. A slot adjacent to or near a wall has the disadvantage of causing inter-stage losses on that wall primarily via the processes of impaction and sedimentation. The apparatus shown in FIGS. 9 and 10 has slots which are symmetric and continuously repeat, and in no case is the longest dimension of any slot adjacent to or near a wall. This is contrasted to a similar impactor having circumferential slots, in which case at least one of the extreme or edge slots must be adjacent to or near a wall, thereby causing inter-stage losses to that wall.

We claim:

1. A sampling apparatus for the collection of particles from a gas containing particles which comprises a first means for directing the flow of said gas toward a second means for collection of at least a portion of said particles by the process of impaction and a third means between and contacting said first and second means and having an innerwall which is a smooth substantially closed curve; said first means containing inlet means radially oriented with respect to said curve of said innerwall of said third means and comprising at least one perforation having a length dimension which is greater than its width dimension; said second means containing outlet means offset from said inlet means in said first means, radially oriented with respect to said curve of said innerwall of said third means and comprising at least one perforation having a length dimension which is greater than its width dimension; said third means being located relative to said inlet means and outlet means and said third means having a configuration such that a substantial number of the streamlines of the flow of said gas after said impaction of at least a portion of said particles in said gas with said second means are in substantial parallelism to the curve of said innerwall of said third means; said first, second and third means forming an enclosed volume having said inlet means in said first means and outlet means in said second means for exit of said gas after said impaction of at least a portion of said particles in said gas with said second means; said outlet means being smaller in size than said inlet means.

2. The apparatus of claim 1 wherein said first means is a plate containing said inlet means and said second means is a plate containing said outlet means.

3. The apparatus of claim 2 wherein the inlet and outlet means each comprises at least one rectangular slot and said third means is an annulus.

4. The apparatus of claim 3 wherein the inlet means comprises four slots wherein the axes of adjacent slots are oriented 90° from each other and wherein said outlet means comprises four slots wherein the axes of adjacent slots are oriented 90° from each other and 45° from any inlet means.

5. The apparatus of claim 4 wherein the enclosed volume contains a hub extending from said first means to said second means and having an outer surface which is a smooth closed curve which is located within the closed curve formed by the inside ends of said radially oriented slots of said inlet and outlet means.

6. A sampling device for the collection of particles from a gas containing particles comprising a plurality of stages in series, each stage comprising a first means for directing the flow of said gas toward a second means for collection of at least a portion of said particles by the process of impaction and a third means between and contacting said first and second means and having an innerwall which is a smooth substantially closed curve; said first means containing inlet means radially oriented with respect to said curve of said inner-wall of said third means and comprising at least one perforation having a length dimension which is greater than its width dimension; said second means containing outlet means offset from said inlet means in said first means, radially oriented with respect to said curve of said inner-wall of said third means and comprising at least one perforation having a length dimension which is greater than its width dimension; said third means being located relative to said inlet means and outlet means and said third means having a configuration such that a substantial number of the streamlines of flow of said gas after said impaction of at least a portion of said particles in said gas with said second means are in substantial parallelism to the curve of said innerwall of said third means; said first, second and third means forming an enclosed volume having an inlet means in said first means and outlet means in said second means for exit of said gas after said impaction of at least a portion of said particles in said gas with said second means; said inlet means of each of said stages decreasing in size from said inlet to said outlet of said device.

7. The device of claim 6 wherein said first means is a place containing said inlet means.

8. The device of claim 7 wherein said second means is a plate containing said outlet means, said inlet and outlet means each comprise at least one rectangular slot and said third means is an annulus.

9. The device of claim 8 wherein the enclosed volume contains a hub extending from said first means to said second means and having an outer surface which is a smooth closed curve which is located at the inside end of said inlet and outlet means.

10. The device of claim 9 wherein the outside ends of said inlet and outlet means are at the innerwall of said third means.

11. The device of claim 8 wherein the inlet means comprises four slots wherein the axes of adjacent slots are oriented 90° from each other and wherein said outlet means comprises four slots wherein the axes of adjacent slots are oriented 90° from each other and 45° from any inlet means.

12. The device of claim 11 wherein the enclosed volume contains a hub extending from said first means to said second means and having an outer surface which is a smooth closed curve which is located within the closed curve formed by the inside ends of said radially oriented slots of said inlet and outlet means.

13. The device of claim 6 wherein said first means and inlet means of each stage after the first stage comprise the second means and outlet means of the next preceding stage.

14. A sampling apparatus for the collection of particles from a gas containing particles which comprises a first means for directing the flow of said gas toward a second means for collection of at least a portion of said particles by the process of impaction and a third means between and contacting said first and second means and having an innerwall which is a smooth substantially closed curve; said first means comprising a plate containing inlet means radially oriented with respect to said curve of said innerwall of said third means and comprising at least one rectangular slot; said second means comprising a plate containing outlet means offset from said inlet means in said first means, radially oriented with respect to said curve of said innerwall of said third means and comprising at least one rectangular slot; said third means comprising an annulus and being located relative to said inlet means and outlet means and said third means having a configuration such that a substantial number of the streamlines of the flow of said gas after said impaction of at least a portion of said particles in said gas with said second means are in substantial parallelism to the curve of said innerwall of said third means; and first, second and third means forming an enclosed volume having said inlet means in said first means and outlet means in said second means for exit of said gas after said impaction of at least a portion of said particles in said gas with said second means; said enclosed volume containing a hub extending from said first means to said second means and having an outer surface which is a smooth closed curve which is located at the inside end of said inlet and outlet means.

15. The apparatus of claim 14 wherein the outside ends of said inlet and outlet means are at the innerwall of said third means.

16. A sampling apparatus for the collection of particles from a gas containing particles which comprises a first means for directing the flow of said gas toward a second means for collection of at least a portion of said particles by the process of impaction and a third means between and contacting said first and second means and having an inner wall which is a smooth, substantially closed curve; said first means containing inlet means radially oriented with respect to said curve of said inner wall of said third means and comprising at least one perforation having a length dimension which is greater than its width dimension; said second means containing outlet means offset from said inlet means in said first means, radially oriented with respect to said curve of said inner wall of said third means and comprising at least one perforation having a length dimension which is greater than its width dimension; said third means being located relative to said inlet means and said outlet means and said third means having a configuration such that a substantial number of the streamlines of flow of said gas after said impaction of at least a portion of said particles in said gas with said second means are in substantial parallelism to the curve of said inner wall of said third means; said first, second and third means forming an enclosed volume having said inlet means in said first means and said outlet means in said second means for exit of the gas after said impaction of at least a portion of said particles in said gas with said second means; said enclosed volume containing a hub extending from said first means to said second means and having an outer surface which is a smooth, closed curve located at the inside ends of said inlet and outlet means.

17. A sampling device for the collection of particles from a gas containing particles comprising a plurality of stages in series, each stage comprising a first means for directing the flow of said gas toward a second means for collection of at least a portion of said particles by the process of impaction and a third means between and contacting said first and second means and having an inner wall which is a smooth, substantially closed curve; said first means containing inlet means radially oriented with respect to said curve of said inner wall of said third means and comprising at least one perforation having a length dimension which is greater than its width dimension; said second means containing outlet means offset from said inlet means in said first means, radially oriented with respect to said curve of said inner wall of said third means and comprising at least one perforation having a length dimension which is greater than its width dimension; said third means being located relative to said inlet means and outlet means and said third means having a configuration such that a substantial number of the streamlines of the flow of said gas after said impaction of at least a portion of said particles in said gas on said second means are in substantial parallelism to the curve of said innerwall of said third means; said first, second and third means forming an enclosed volume having an inlet means in said first means and outlet means in said second means for exit of said gas after said impaction of at least a portion of said particles in said gas with said second means; said enclosed volume containing a hub extending from said first means to said second means and having an outer surface which is a smooth, closed curve which is located at the inside ends of said inlet and outlet means; the inlet means of each of said stages of said device decreasing in size from the inlet to the outlet of said device.

* * * * *